Jan. 20, 1942 P. R. WHITTIER Plant Pat. 499

DIANTHUS

Filed May 2, 1941

Witness
Addison E. Avery

INVENTOR
PAUL RUSKIN WHITTIER
BY John H. Lawrence,
HIS ATTORNEY

Patented Jan. 20, 1942

Plant Pat. 499

UNITED STATES PATENT OFFICE

499

DIANTHUS

Paul Ruskin Whittier, Beverly, Mass., assignor to The Wayside Gardens Company, Mentor, Ohio, a corporation of Ohio Application May 2, 1941, Serial No. 391,567

1 Claim. (Cl. 47—60)

This invention relates to a new variety of dianthus which is a perennial and has been asexually reproduced true to form in considerable quantities, particularly in and around Beverly, Massachusetts, the place of its origin, at Keene, New Hampshire, and at Mentor, Lake County, Ohio.

The new variety is a hybrid pink of which the ancestry is as follows:

*I. First generation*

1. *Seed parent.*—A Dianthus seedling known as "extra hardy Scotch Paisley pink" which originated in Surrey, England, and is a hardy plant which grows about twelve inches high and has stiff stems with semi-double flowers with a red center.

2. *Pollen parent.*—*Dianthus allwoodii,* which has bright pink flowers.

*II. Second generation*

3. *Seed parent.*—The seed parent of the first generation.

4. *Pollen parent.*—A cross having a salmon pink blossom and resulting from the crossing of the first generation seed parent and the first generation pollen parent.

*III. Third generation*

5. *Seed parent.*—A cross having a semi-double blossom, i. e., only two rows of petals, and resulting from crossing the second generation seed parent and the second generation pollen parent.

6. *Pollen parent.*—A cross having true double blossom and resulting from crossing the second generation seed parent and the second generation pollen parent.

The third generation plants are the parents of the present plant.

The plant was developed and first discovered and grown and asexually reproduced by Paul Ruskin Whittier at Beverly, Massachusetts. The first asexual reproduction was from cuttings made and planted in the fall of 1937 and which bloomed in 1938. Thereafter, the plant was placed in test fields for purposes of testing for Paul Ruskin Whittier its characteristics and its suitability for the market.

Figure 1:
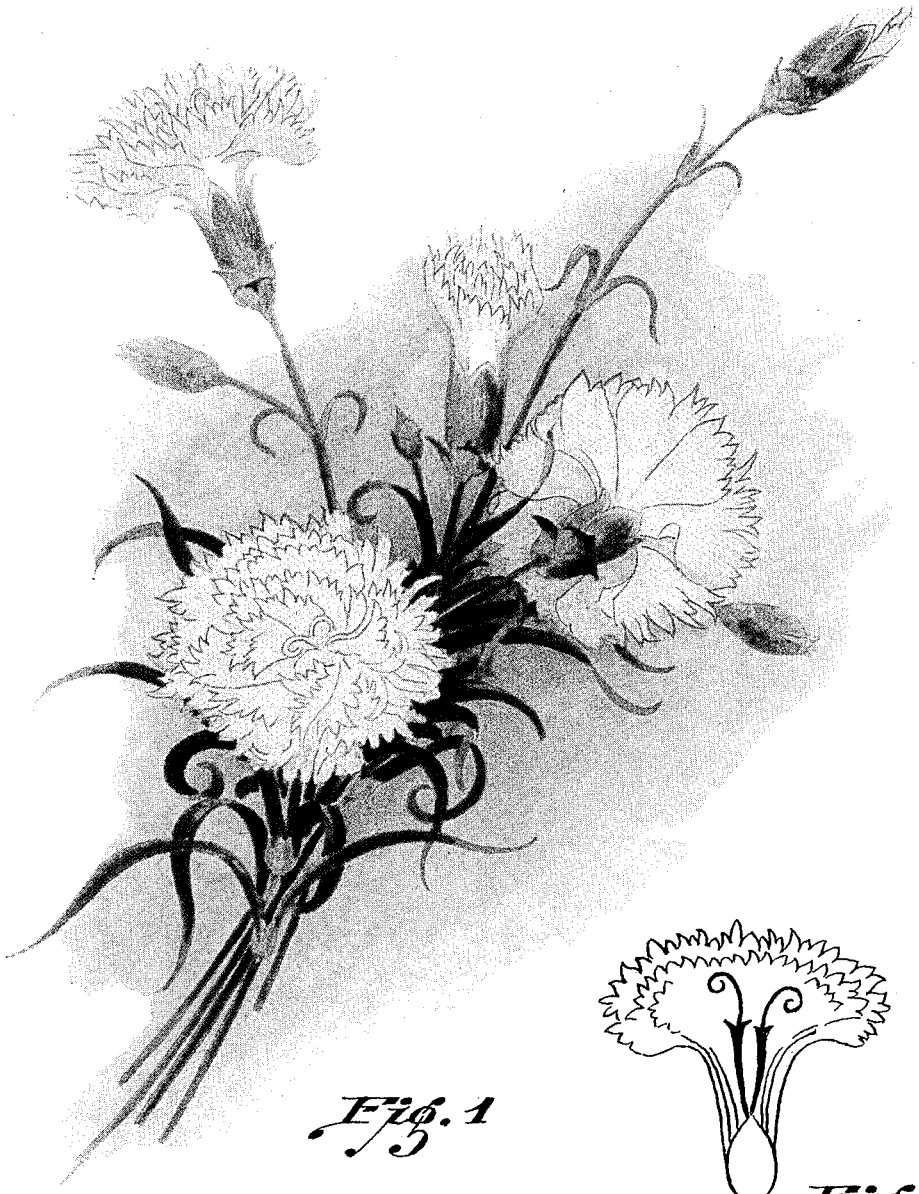
Figure 2:
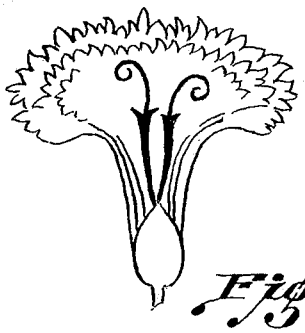

Fig. 1 is an illustration of the plant, the root system and part of the stems being omitted; Fig. 2 is a longitudinal sectional view of one of the flowers of the plant.

The root of the plant is in the form of a fibrous mass of average size for the particular type of plant. The root structure generally has good characteristics of disease and drought resistance and is exceptionally resistant to wetness. The winter resistance of the roots is good when the roots are protected, and fair when unprotected, the roots having withstood observed temperatures as low as 15° below zero. The root system does well in sandy loam and fairly heavy loam, the only types of soil as to which observations have been made.

The exposed plant is herbaceous, generally upright, and rather dense or compact, growing to a height of about twelve inches, and in a two-year old plant, having a spread of about ten inches. It is of regular contour and a vigorous and healthy grower. The exposed plant has good resistance to low temperatures, when protected, and a fair resistance, when unprotected. Its resistance to disease and drought are good and resistance to wet seasons is very good. It does well in moderate sun. No observations have been made as to its behavior under varying conditions of shade and various types of exposures. It grows well in soil of normal drainage.

The main stalks of the plant are upright, long, wiry, thin, herbaceous, and generally adequate to support the foliage and bloom. They are approximately twice as long as the stems of most of the *Dianthus plumarius* hybrids, such as the "Essex Witch" and "Her Majesty," both now in general commerce. In color, the new growth is a light silvery green, the older growth being a darker silvery green comparable to Maerz & Paul Chart No. 24–L–4. The stalks have a smooth surface texture and the manner of growth from the roots is that usual for this type of plant.

The foliage is compact with leaves arranged oppositely in pairs, and the pairs are placed alternately 90° from each other about the stem and abundant in quantity. They are silvery green comparable to Maerz & Paul Chart No. 24–L–4, and at the bases and adjacent the joints they are a light green comparable to Maerz & Paul Chart No. 19–L–6. The color otherwise generally is uniform. The leave are of medium size, lanceolate, of medium thickness and smooth textured on both surfaces. Their persistency on the plant is excellent.

The plant blooms well in the sun, and no observation has been made as to the effect of other exposures on its blooming habits. It blooms well in wet or dry seasons and likewise in cold seasons. The blooming period begins and is heavy in late spring and early summer, but the plant blooms recurrently thereafter throughout the entire summer. The number of blooms is increased if the blossoms are cut as they appear. The buds are of normal size for the type of plant and are supported in upright position on their stems. The petals are pink, comparable to Maerz & Paul Chart No. 2–E–4, when the sepals first divide and become darker when the petals begin to unfurl. When the plant is half blown, the petals are pink comparable to Maerz & Paul Chart No. 1–K–5. The flowers open more rapidly in hot weather and are retarded in the rate of opening by cool weather. The bloom is large for a hardy pink and ranges from about 1¾ inches to 2¼ inches in diameter. Generally they are borne singly on the terminal of the main stalks and sometimes, but rarely, in pairs, the other bloom in such instances being borne on a side branch near the terminal of the main stalk. Their permanence on the blooming plant is good and their permanence when cut is excellent.

The blossoms, while fully double, do not contain so many petals that they split the calyx. From all observations made to date, the appears that the characteristic that the calyx of the flower never splits is different from the characteristics of hardy pinks having double blossoms, of which the calyx usually splits.

Each blossom has about eighteen to twenty petals, the color thereof being comparable to Flirt, Maerz & Paul Chart No. 2–K–9, when the bloom is partly opened and comparable to Rose d'Althoea, Maerz & Paul Chart No. 1–I–7, when fully opened. In general, the color is a shade deeper than the carnation known as "Giant Laddie."

The color of the petals is generally comparable to Rose d'Althoea, Maerz & Paul Chart No. 1–I–7, at the outer edges, shading toward watermelon pink, comparable to Maerz & Paul Chart No. 1–K–9 from the outer edges inwardly toward their bases. There is little or no difference in color between the central petals and the outer petals of the bloom.

The reverse of the petals is Blossom or Venetian pink comparable to Maerz & Paul Chart No. 2–F–7, and several shades lighter than the upper surface with a tendency toward whiteness toward their centers. Near the base of the petals just exposed above the sepals both surfaces of the petals tend toward whiteness, this being visible from the under surface of the petals but not noticeable in the upper surface of a normal bloom except at the center upon close observation. The deep pit shadows are a darker color, comparable to Maerz & Paul Chart No. 2–L–9.

The general tonality of the flower from a distance is salmon pink and there is little change in color during the blooming season except toward the very end of the season the color tends toward a lighter salmon pink.

The petals are of smooth texture. They are slightly concave toward the center of the plant, some of the outer petals having a tendency to be slightly recurvent. They have sharply serrated outer margins, the serrations often being compound or having crests with secondary serrations, thus having a tendency toward or appearance of fimbriation. They are rather thin, generally circular or widely oval on the main portion with long tapering bases which are relatively narrow pointed downwardly beginning from the top of the sepals to the base thereof. A portion of the petals is slightly crinkled. They are imbricated in arrangement about the center. There are no petaloids on the flower and the persistence of the petals on the flower is very good both in the cut and uncut flowers. The fragrance is strong and similar to the well known greenhouse carnation. Its lasting quality on both the cut and uncut flowers is excellent. The stamens are simple, cream color, and each flower has about seven or eight filaments of medium length and white, the anther being cream. Both the styles and stigmas are rather tall and white. The calyx is white. The ovaries are arranged from sparse to medium. The resultant fruit is of the usual form and color at maturity and is present in the usual amount.

In general, the plant combines the best qualities of both Dianthus and Carnation. The plant is outstanding because of the size, form, fragrance and color of the blossoms, and the fact that though the blossom is double, the calyx does not split; its very long, wiry, thin stems; the bearing of the buds generally singly or, at most, in pairs, on the main stalks; its persistency in blooming, and its delightful, strong and lasting fragrance; its vigorous growth, general sturdiness, and neatness of growth; the resistance of the roots to wetness; the persistency of the leaves on the plant, and the permanence of the petals on the cut flower.

Each of the above characteristics of the plant and the combinations of part or all thereof, I claim distinguish the new variety from all other known varieties of Dianthus.

I claim:

The new variety of Dianthus herein shown and described characterized in the outstanding color, size, form and fragrance of the flower, the general neatness of the plant as a whole, the ease of growth of the plant and the fact that the calyx of the flower does not split.

PAUL RUSKIN WHITTIER.